(12) United States Patent
Burmeister

(10) Patent No.: US 11,457,991 B2
(45) Date of Patent: Oct. 4, 2022

(54) ELASTIC MOUNTING CLAMP

(71) Applicant: AESCULAP AG, Tuttlingen (DE)

(72) Inventor: Christoph Burmeister, Singen (DE)

(73) Assignee: AESCULAP AG, Tuttlingen (DE)

( * ) Notice: Subject to any disclaimer, the term of this patent is extended or adjusted under 35 U.S.C. 154(b) by 420 days.

(21) Appl. No.: 16/610,562

(22) PCT Filed: May 8, 2018

(86) PCT No.: PCT/EP2018/061873
§ 371 (c)(1),
(2) Date: Nov. 4, 2019

(87) PCT Pub. No.: WO2018/206579
PCT Pub. Date: Nov. 15, 2018

(65) Prior Publication Data
US 2020/0146767 A1 May 14, 2020

(30) Foreign Application Priority Data
May 8, 2017 (DE) .................... 10 2017 109 869.0

(51) Int. Cl.
*A61B 50/20* (2016.01)
*A61L 2/26* (2006.01)

(52) U.S. Cl.
CPC ............ *A61B 50/20* (2016.02); *A61L 2/26* (2013.01); *A61L 2202/24* (2013.01)

(58) Field of Classification Search
CPC ......... A61B 50/20; A61B 50/33; A61B 50/22; A61B 50/34; A47L 15/505; A61L 2/26;
(Continued)

(56) References Cited

U.S. PATENT DOCUMENTS 992,047 A * 5/1911 Peak ...................... B42F 17/02
40/658
1,322,791 A * 11/1919 Hormes .................. B65D 1/36
211/184

(Continued)

FOREIGN PATENT DOCUMENTS

| DE | 102004008455 B3 | 8/2005 |
| DE | 202005016771 U1 | 1/2006 |
| DE | 102007030863 A1 | 1/2009 |

OTHER PUBLICATIONS

German Search Report for German Application No. 10 2017 109 869.0, with English translation, dated Oct. 20, 2017, 16 pages.

(Continued)

*Primary Examiner* — Jennifer E. Novosad
(74) *Attorney, Agent, or Firm* — Christopher A. Rothe; Culhane Meadows, PLLC

(57) ABSTRACT

A securing device secures a mounting for sterile products or products to be sterilized in a medical container. The securing device has a first securing section, in particular a U-shaped or hook-shaped securing section, which is designed to engage around an edge of a first recess provided on the base of the container in a form-fitting manner, and a second securing section, which is designed to engage around the edge of the first recess and/or at least one second recess in a form-fitting manner from the opposite direction. At least one of the two securing sections is designed to be spring-elastic in order to allow the securing device to be clamped to the base of the container.

19 Claims, 4 Drawing Sheets

(58) Field of Classification Search
CPC .......... A61L 2202/24; Y10T 403/4628; Y10T 403/4631; Y10T 403/4662; Y10T 403/4674; A47B 57/58; A47B 57/588; A47B 96/04; A47B 65/10; A47F 5/005; A47F 7/144; A47F 3/12; F16B 2/22
USPC ..... 211/85.13, 184; 206/477, 478, 480, 481, 206/483, 479; 422/297, 300; 248/220.31, 220.41, 220.42, 220.43, 248/221.11, 224.8, 225.21; 403/240, 241, 403/252, 256
See application file for complete search history.

(56) References Cited

U.S. PATENT DOCUMENTS

| | | | | |
|---|---|---|---|---|
| 1,608,401 | A * | 11/1926 | Kress | A47F 3/12 211/184 |
| 1,721,529 | A * | 7/1929 | Hatfield | B42F 17/02 211/184 |
| 1,734,407 | A * | 11/1929 | Taussig | A47F 5/005 248/248 |
| 1,767,823 | A * | 6/1930 | Vanderveld | A47F 5/005 248/248 |
| 1,770,942 | A * | 7/1930 | Morris | A47F 5/005 211/184 |
| 1,978,501 | A * | 10/1934 | Meyer | A47F 5/005 24/458 |
| 3,154,281 | A * | 10/1964 | Frank | H05K 3/301 248/220.31 |
| 3,497,081 | A * | 2/1970 | Field | A47B 57/58 211/184 |
| 3,501,019 | A * | 3/1970 | Armstrong | A47B 57/58 211/184 |
| 3,545,711 | A * | 12/1970 | Scheneman | A47F 5/0823 248/223.31 |
| 3,698,568 | A * | 10/1972 | Armstrong | A47F 5/005 211/184 |
| 3,703,964 | A * | 11/1972 | Field | A47F 5/005 24/537 |
| 3,751,575 | A * | 8/1973 | Barb | H04Q 1/142 248/222.12 |
| 3,836,105 | A * | 9/1974 | Marschak | A47F 7/00 455/67.11 |
| 3,853,293 | A * | 12/1974 | Larson | A47F 5/0823 248/222.12 |
| 4,135,868 | A * | 1/1979 | Schainholz | A61L 2/26 422/310 |
| 4,193,198 | A * | 3/1980 | Bauer | A61C 19/02 211/DIG. 1 |
| 4,887,783 | A * | 12/1989 | Franklin | A47F 5/0815 248/225.11 |
| 4,898,354 | A * | 2/1990 | Whittington | A47B 57/585 211/175 |
| 4,976,058 | A * | 12/1990 | Valiulis | A47F 5/0869 40/657 |
| 5,384,103 | A * | 1/1995 | Miller | A61L 2/26 206/508 |
| 5,433,930 | A * | 7/1995 | Taschner | A61B 50/34 206/370 |
| 5,454,534 | A * | 10/1995 | Baskas | B26B 5/00 248/176.1 |
| 5,492,671 | A * | 2/1996 | Krafft | A61L 2/26 422/26 |
| 5,732,916 | A * | 3/1998 | Gordon | B60K 37/04 248/220.31 |
| 5,759,502 | A * | 6/1998 | Spencer | A61L 2/26 206/370 |
| 5,843,387 | A * | 12/1998 | Dane | A61L 2/26 206/483 |
| 5,848,714 | A * | 12/1998 | Robson | A61B 17/06061 211/85.13 |
| 5,918,749 | A * | 7/1999 | Pille | A47L 15/505 211/41.9 |
| 6,003,685 | A * | 12/1999 | Malin | A47F 5/0861 248/220.42 |
| 6,015,124 | A * | 1/2000 | Loy | A47F 5/0815 40/607.13 |
| 6,082,687 | A * | 7/2000 | Kump | G09F 17/00 248/224.51 |
| 6,193,932 | B1 * | 2/2001 | Wu | A61L 2/07 206/439 |
| 6,244,447 | B1 * | 6/2001 | Frieze | A61L 2/26 206/370 |
| 6,331,280 | B1 * | 12/2001 | Wood | A61L 2/26 206/268 |
| 6,382,575 | B1 * | 5/2002 | Frush | A61L 2/26 211/85.13 |
| 6,419,886 | B1 * | 7/2002 | Oberdorfer | A61L 2/26 422/292 |
| 6,436,357 | B1 * | 8/2002 | Frieze | A61L 2/26 422/292 |
| 6,481,678 | B1 * | 11/2002 | Chong | H02G 3/288 248/220.42 |
| 7,722,837 | B2 * | 5/2010 | Riley | A61B 50/33 206/370 |
| 8,069,998 | B2 * | 12/2011 | Thomas | A61B 50/34 206/370 |
| 8,087,519 | B2 * | 1/2012 | Bramley | A47L 15/505 211/41.3 |
| 8,157,230 | B2 * | 4/2012 | Krueger | A47B 96/068 248/222.51 |
| 8,267,246 | B2 * | 9/2012 | Bettenhausen | A61B 50/30 206/439 |
| 8,272,508 | B2 * | 9/2012 | Bettenhausen | A61L 2/26 206/370 |
| 8,453,984 | B2 * | 6/2013 | Best | F24C 15/16 248/222.12 |
| 8,827,088 | B1 * | 9/2014 | Krause | A61L 2/00 211/85.13 |
| 8,899,424 | B2 * | 12/2014 | Bayazit | H04Q 1/064 248/220.31 |
| 9,193,063 | B2 * | 11/2015 | Huang | F16B 2/14 |
| 9,326,604 | B1 * | 5/2016 | Schuldt | A47B 96/021 |
| 9,636,429 | B2 * | 5/2017 | Cushion | A61L 2/00 |
| 10,391,190 | B2 * | 8/2019 | Oko | F16B 5/0614 |
| 10,398,239 | B1 * | 9/2019 | Luberto | A47F 5/0025 |
| 10,575,933 | B2 * | 3/2020 | Berg | A61B 50/33 |
| 10,618,159 | B2 * | 4/2020 | Maruzzo | A47B 88/994 |
| 11,090,127 | B2 * | 8/2021 | Oko | A61B 50/33 |
| 2004/0011754 | A1 * | 1/2004 | Zadak | A47B 57/588 211/175 |
| 2007/0212277 | A1 * | 9/2007 | Riley | A61B 50/34 206/370 |
| 2010/0176016 | A1 * | 7/2010 | Pell | A61B 50/33 206/370 |
| 2012/0085720 | A1 | 4/2012 | Bettenhausen et al. | |
| 2013/0319888 | A1 * | 12/2013 | Birkbeck | A61B 50/30 206/370 |
| 2014/0083886 | A1 * | 3/2014 | Winterrowd | A61B 50/34 206/370 |
| 2015/0151017 | A1 * | 6/2015 | Tipton | A61L 2/26 422/310 |
| 2020/0146767 | A1 * | 5/2020 | Burmeister | A61L 2/26 |
| 2021/0338357 | A1 * | 11/2021 | Lenzenhuber | A61B 50/3001 |
| 2021/0386499 | A1 * | 12/2021 | Bailey | A61B 50/33 |

OTHER PUBLICATIONS

International Search Report and Written Opinion for International Application PCT/EP2018/061873, dated Jul. 24, 2018, 9 pages.

* cited by examiner

ELASTIC MOUNTING CLAMP

CROSS REFERENCE TO RELATED APPLICATIONS

This application is the United States national phase entry of International Application No. PCT/2018/061873, filed May 8, 2018, which claims the benefit of priority of German Application No. 10 2017 109 869.0, filed May 8, 2017. The contents of International Application No. PCT/2018/061873 and German Application No. 10 2017 109 869.0 are incorporated by reference herein in their entireties.

FIELD

The invention relates to a securing device/elastic mounting clamp, which is held in a form-fitting manner in the perforation or the openings of a sterilization basket by a spring force type biasing means and to which a depositing device/mounting or a receiving element for the arrangement/mounting of goods to be sterilized can be attached in the interior of a sterilization basket.

The invention further relates to a mounting device with such a depositing device, which can be attached to a sterilization mesh basket by means of one or more securing devices.

The invention also relates to a modular mesh basket system with a sterilization mesh basket, which can be equipped as required with a number of different depositing devices for different sterile products.

The sieve baskets described above, which may additionally include a lid, are used for example in hospitals, clinics, laboratories or similar facilities for the sterilization of corresponding goods/instruments. In addition, the sieve baskets can be used for storage, safe transport, organization or the like of the goods/instruments. For sterilization, the goods placed in a mesh basket are placed in a sterilizer together with the mesh basket.

BACKGROUND

By way of example, sterilization mesh baskets are known from prior art which comprise securing devices and mounting devices as they are shown in DE 10 2004 008 455 B3 and DE 20 2005 016 771 U1. The generic mounting devices disclosed there substantially consist of a web which has at least one receptacle for a product to be sterilized and can be detachably attached to the mesh basket via a fastening system. The mounting devices serve as a mounting for various medical goods, and in the embodiment shown, substantially rod-shaped surgical instruments can be inserted therein transversely to the longitudinal extension of the webs. Especially during the transport of the mesh basket, it may be exposed to vibrations. With this state of the art, the sterile products may slip out of the mounting device on the one hand, and on the other hand it may be damaged by stronger vibrations. In addition, the depositing devices or webs are attached to the side walls of the sterilization basket in this disclosure. With such a solution, the length of the mounting devices must be adapted to the dimensions of the mesh basket, and it is often necessary that the web of the mounting extends across the entire width of the mesh basket to provide sufficient stability by a bilateral fastening. As a result, each mounting device must be individually constructed and produced for the respective set or mesh basket, which means a considerable effort and prevents subsequent modification of the mesh basket configuration.

The state of the art also knows mounting devices with fastening in the side walls, in which the webs are firmly connected to the mesh basket by welding or riveting, which, in addition to the disadvantages described above, prevents the arrangement in the mesh basket from being subsequently changed.

In addition, the state of the art also knows fastening systems for securing the individual webs in the base of the mesh basket. Already known solutions use screw/nut connections or fastening pins to anchor the webs in the base, e.g. by means of feet or bent sections provided at lower portions of the same. Such systems have the disadvantage of being comparatively complex in their assembly and disassembly and, without stamping the bars or other constructive measures, offering only a comparatively low stiffness, which can be a disadvantage in particular when taking up heavy instruments, such as orthopedic instruments. In addition, for loosening the fasteners of such state of the art solutions, usually access to the underside of the mesh basket is required, e.g. to loosen a nut or release the form fit of a fastening pin, which is not always possible on the one hand and not ergonomic on the other hand.

SUMMARY

In view of the above-mentioned state of the art, the task of the present invention is to provide a generic securing device for securing a depositing device, for receiving or arranging/holding parts to be sterilized in a mesh basket, which allows the configuration of the mounting devices in the mesh basket to be flexibly adapted or facilitates an individual loading of a mesh basket also with mounting devices in web shape and can be used for different mesh basket variants.

Furthermore, the preferred object of the invention is to allow an exchange of the securing devices as well as the depositing devices also in retrospect. In particular, it is a preferred aim that such an exchange is also possible if the user only has access to the mesh basket from above, because the mesh basket is already in the sterilizer, for example, and access to the bottom of the basket is thus prevented. Another preferred aim of the invention is that the securing device can be attached to the container without tools and with little space requirement and the depositing devices can be attached to one or more securing devices without tools and with little space requirement.

Another preferred aim of the present invention is to provide securing devices that provide the mounting devices with sufficient stability/stiffness, even if they are fixed on the base, as the case may be, with only one single securing device. In particular, the object of the present invention is to ensure that each individual securing device per se provides sufficient stability against tilting of the securing device in the fixed state.

In accordance with a first aspect of the invention, a securing device or elastic mounting clamp for securing a depositing device for sterile products or products to be sterilized (e.g. surgical instruments or implants) in a medical container, in particular a sterilization basket is proposed.

For this purpose, the securing device comprises a supporting/receiving base (16) for supporting/receiving the sterile product mounting (11), which has an undercut portion acting in a first direction and a first securing section as a fixed bearing, which is designed to be brought into a latching engagement with a corresponding undercut on the medical container.

In addition, the securing device comprises an undercut element movably held on the supporting/receiving base in a direct or indirect manner, and a second securing section as a floating bearing, which acts in a second direction directed contrary to the operating direction of the undercut portion and is designed to be brought into a latching engagement with a corresponding undercut on the medical container and can be biased into the second direction by means of a spring element or a spring portion on the undercut element or on the supporting/receiving base while being directly or indirectly supported on the supporting/receiving base. This has the advantage that the securing device according to the invention can be fixed on the container and detached from it again without any tools, and no further fastening elements such as screws, nuts or fastening pins are required for fixing.

Preferably, the first securing section is designed to engage around an edge of a first recess/breakthrough in the base of the container, or a wall section bordering the first recess/breakthrough, in a foam-fitting manner. In addition, preferably the second securing section is designed to engage around the edge of the first recess and/or an edge of at least one second recess in a form-fitting manner from the opposite direction. In other words, the first and the second securing section, in a state in which the securing device is secured to the container, are able to encompass the edges of recesses provided in the base of the container in each case from opposite directions, in order to provide a supporting form fit. In order to be able to transfer the securing device from a state fastened to the container to a state detached from the container and vice versa, it is preferable to design at least one of the two securing sections so as to be spring-elastic, so that with an elastic deformation of the at least one resilient securing section the form fit between the securing device and the container base cab be released, or the securing device in the elastically deformed state can be inserted in recesses of the container base and after insertion is held/clamped in a form-fitting manner in the base by the spring-elastic restoring forces. Such an embodiment immobilized by holes in the base of the container has the advantage of allowing a more flexible arrangement of the securing device and thus of the mounting in the container.

According to another preferred embodiment, a holding section on the supporting/receiving base may be provided, which is designed to hold the sterile product mounting in a form-fitting manner. This has the advantage that a tool-free fixation, releasing and/or exchanging of various depositing devices, which may be adapted for receiving/arranging different sterilization goods, is possible on one or more securing devices. Preferably, the holding section can be further designed such that the sterile product mounting, if the supporting/receiving base is attached to the base of the container, can be inserted into the holding section perpendicularly to the extending direction of the base. In other words, the securing device may be designed in such a way that the sterile product mounting can be inserted vertically into a supporting/receiving base pre-assembled on the container base. This has different advantages. For one thing, the possibility of vertically inserting the sterile product mounting into the supporting/receiving base reduces the lateral space required for assembly. On the other hand, with web-like sterile product mountings, the same supporting/receiving base is able to accommodate mountings with differing web lengths. This means that the supporting/receiving base can be adapted for different sterile product mountings. Especially preferred is a securing device which has two supporting/receiving bases, which are each designed to accommodate one end portion of a web of a sterile product mounting.

According to another preferred embodiment, the holding section may be designed as a sheet metal bent section which has substantially U-shaped legs between which the sterile product mounting, in particular with web-like or plate-like sections, can be inserted and held. This allows easy manufacturing of the holding section on the supporting/receiving base by sheet metal forming Such a U-shaped bent section also offers a high stability with the possibility of vertical insertion. In addition, the ends of the opening of the U-shape can serve as a lateral stop for an inserted depositing device.

To secure the depositing device against being pulled out of the bent section, additionally a pin/bolt may preferably be provided, which can be arranged in a common hole of holding section and depositing device.

According to another preferred embodiment, the undercut element can be realized as a spring element which has one end portion that is designed to enter a form fit with the medical container and another end portion which is supported by the sterile product mounting held in the holding section and thus clamps the latter in place in the holding section. In other words, the second securing section (the undercut element) can be clamped between the perforation in the container base and a depositing device held in the holding section in such a way that, by the spring force thus exerted, both the first securing section (undercut portion of the supporting/receiving base) is held in a form-fit connection with the container base and the depositing device in the holding section is additionally held in a frictional manner.

According to a preferred embodiment of the invention, the depositing device may have a holding section on which the depositing device for the sterile products is mounted or can be mounted, and the two depositing sections, preferably at the level of the container base and spaced from the holding section substantially in the same direction, may engage in recesses of the container base. This has the advantage that by being locally close to the points of engagement, a securing device according to the invention can be adapted to be detached from the container base with one hand; furthermore, the space required for attaching the securing device to the container base can be kept to a minimum. Spacing the securing sections from the holding section also has the advantage that a lever arm in regard to sterile products stored in the depositing device can be increased, which can increase the stability of the fixation.

According to another preferred embodiment, the two securing sections can engage in the same recess or in adjacent recesses in the container base in order to further reduce the space required for mounting the securing device on the container base. Such a compact arrangement of the securing sections or their points of engagement in the container base also makes it easier to fix the securing section in any orientation (i.e. in one of the four directions of the side walls).

According to another advantageous embodiment, the sterile product placed on the depositing device can be spaced in the opposite direction relative to the holding section to use the lever arm formed by the spacing of the securing sections from the holding section. In other words, viewed from above, in the case of a securing section attached on the container and having a depositing device attached thereto, the holding section may lie between the center(s) of gravity of the sterile product to be stored and the points of engagement of the securing sections, or may even form a point of symmetry or plane of symmetry thereto.

According to a preferred development of the invention, the first securing section in the event of a container having a sieve-like or lattice-shaped base, such as a sterilization mesh basket—may be designed to grasp a bar of the lattice-shaped base in a form fighting manner. The second securing section may be designed in such a case to encompass the same lattice bar from an opposite direction in a form-fitting manner. Advantageously, the first and the second securing section can encompass the lattice bar in such a way that they form a closed profile in a cross-sectional view/side view or completely enclose the lattice bar in its circumference once. Such a design of the invention allows an even more compact design of the securing device.

According to a preferred embodiment, the first securing section can be formed as a hook or U-shaped bent section and can first be inserted in the first recess in the container base and then be moved, preferably shifted, to a securing position in which it engages around the edge of the first recess or the lattice bar in such a form-fitting manner that it can only be released from the form fit in a preferential direction. With such an embodiment, the second securing section can be spring-elastic and adapted to be brought into engagement with at least one further recess or lattice bar in such a way that the securing device is acted upon with a spring force contrary to the preferential direction.

According to a preferred design of the invention, the second securing section is able to produce a form fit transverse to the preferential direction by resting against at least two edges of recesses in the base in the attached state, preferably two edges which are substantially parallel to the preferential direction.

According to another preferred embodiment, the second securing section may be forked and hold two edges of recesses in the base in a form-fitting manner between its fork prongs in a form-fitting manner or may be held between two edges of recesses in the base in a form-fitting manner to make a form fit transverse to the preferential direction. In this way, a backlash of the securing device transverse to the preferential direction (along the edge/lattice bar embraced by the first securing section) can be minimized while taking up little space. Preferably, such a forked embodiment makes it possible that the second securing section laterally engages around the first securing section to save space and engages below recesses or the lattice bar, similar to a forklift, to create an additional form fit.

According to a preferred embodiment of the invention, both the first and the second securing section in the attached state are arranged on the container inside and engage the recess or recesses from the container inside, so that the securing device is attachable and detachable exclusively with access from the container inside, i.e. without requiring access from a container underside.

According to further preferred design, the securing device may form a support area with which it rests on the container base, wherein preferably the holding section may rest on one end of the support area and the securing sections can engage in the perforation of the container base at the opposite end of the support area. With such a support area, the stability of the securing device can be increased in regard to a tilting movement.

Preferably, the support area may form an extension that projects beyond the point of engagement of the first and/or second securing section in the container base and is adapted to establish a contact with the container base that supports the securing device against tilting.

According to a preferred embodiment, the second securing section can be detachably connected to the securing device. In this context, the second securing section is held in a form-fitting manner on the securing device preferably by means of a pin (or the pin holding the depositing device in the form fit) and is held in a force-fitting manner on the securing device via its internal elastic restoring forces. A modular design of the second securing section can facilitate the fastening and unfastening of the securing device to/from the base and enables an exchange of the second securing section, e.g. in case of a defect or to adapt it to a different lattice structure of another mesh basket variant.

According to a preferred design, the securing device can be made of a medically approved material with a high resistance to changing temperature and pressure loads, preferably a medical stainless steel or aluminum. The second securing section preferably consists of a medical spring steel.

According to a further aspect of the invention, a mounting device is provided which comprises one or several securing sections according to the invention, on which one or more depositing devices for receiving/arranging sterile products can be arranged. This has the advantage that for different sterilization goods, e.g. surgical instruments, adapted depositing devices can be developed/manufactured, which all are designed to be received by one or more securing devices according to the invention or to be attachable to one or more securing devices. This means that a mounting device according to the invention allows, with a few variants of securing devices, to fix a multitude of different depositing device variants for various sterilization goods to medical containers in a flexible manner and without tools.

Another aspect of the invention relates to a modular mesh basket system for arranging/receiving sterile products or products to be sterilized, comprising
- a mesh basket, in particular a sterilization mesh basket, comprising an interior defined by a base and side walls and having a number of recesses in the base; and
- a number of mounting devices, which can be brought into engagement with the recesses and are built up in modular fashion from depositing devices and securing devices. According to the invention, the securing devices can be brought into engagement with the perforation of the mesh basket base in a flexible manner and may be adapted to accommodate different depositing devices.

According to an advantageous further development, the perforation of different mesh baskets can be designed in such a way that securing devices according to the invention can be used for mesh baskets in an overarching way, i.e. for mesh baskets of different systems and with different dimensions.

BRIEF DESCRIPTION OF THE DRAWING FIGURES

The invention is explained in more detail below using preferred exemplary embodiments with reference to the accompanying Figures wherein.

DETAILED DESCRIPTION

Figure 1:
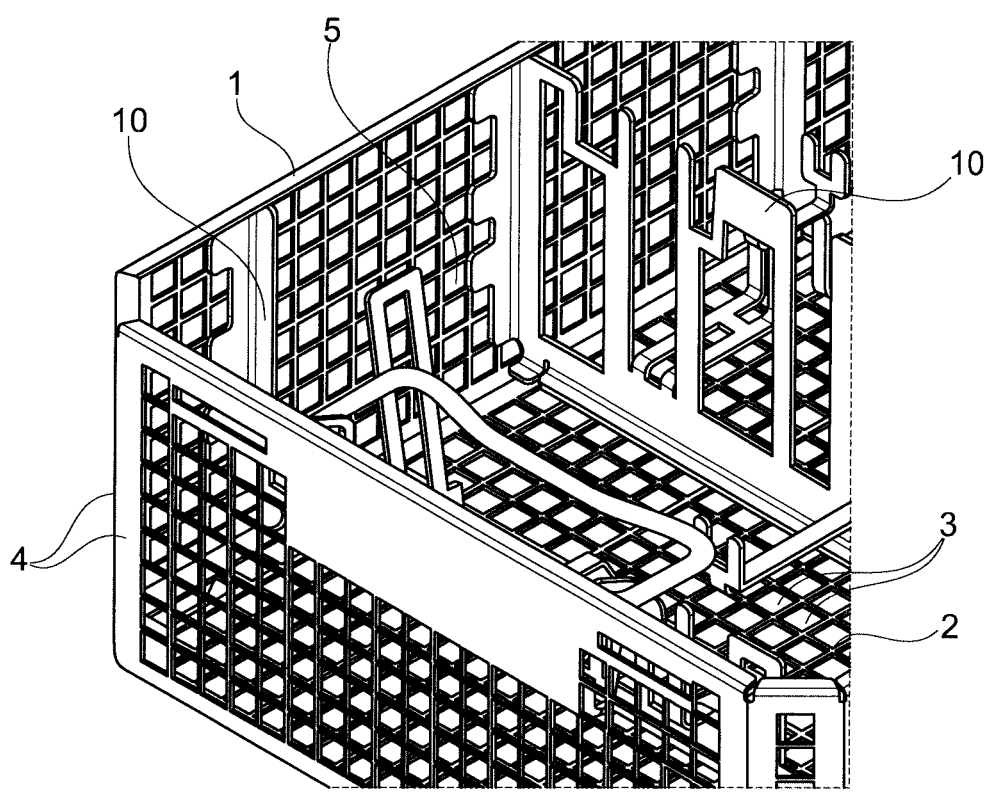
FIG. 1 is a perspective view of a mesh basket with prior art mounting devices immobilized on its side walls.

FIG. 1 shows a mesh basket 1 as it is used as an insert in sterilization containers for sterilizing surgical elements and the like. The sieve-like base 2 has a large number of recesses/apertures 3.

The mounting devices 10 shown in FIG. 1 correspond to the state of the art and are attached to the side walls of the mesh basket 1, in the example shown by welding the lateral front sections of the web-like mounting devices 10 to the side walls 4 of the mesh basket 1. The mounting devices 10 may have a multitude of depositing devices 11 for the arrangement/receiving of various surgical instruments and other sterile products. These depositing devices can basically be adapted as desired to the geometry of the sterile products to be arranged or stored and, for example, form recesses and/or cantilevered portions or support devices. The illustrated embodiment with fixation of the mounting devices 10 in the side walls 4 of the mesh basket has the disadvantage that the mounting devices 10 usually extend from a side wall 4 of the mesh basket 1 to the opposite side wall which is why using such a mounting device 10 with a mesh basket 1 with other dimensions is not possible. As a consequence, new mounting devices 10 must often be designed and manufactured individually for each new mesh basket variant.

Figure 2A:
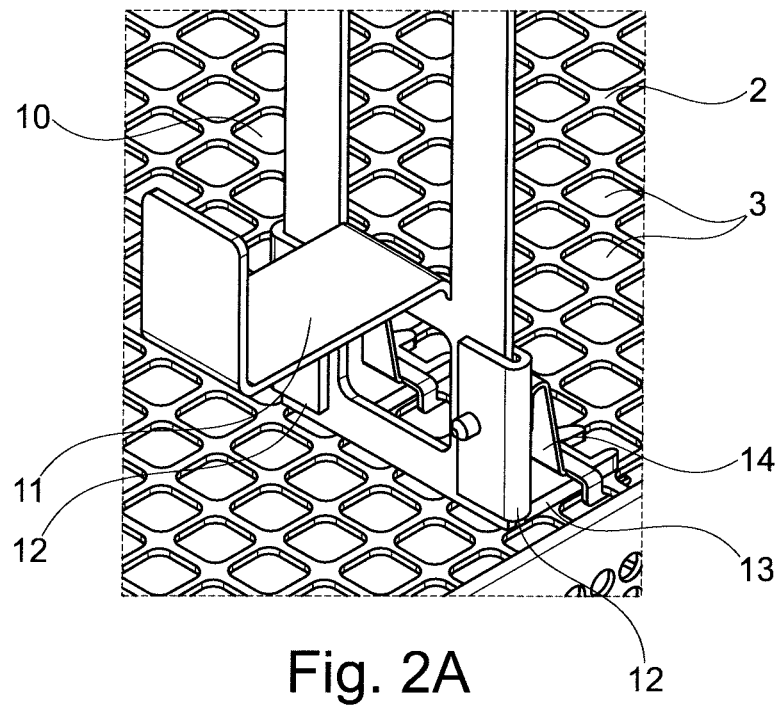
FIG. 2A is a back view of a mounting device according to the invention comprising a securing device according to the invention which is fixed in the perforated base of a mesh basket.
Figure 2B:
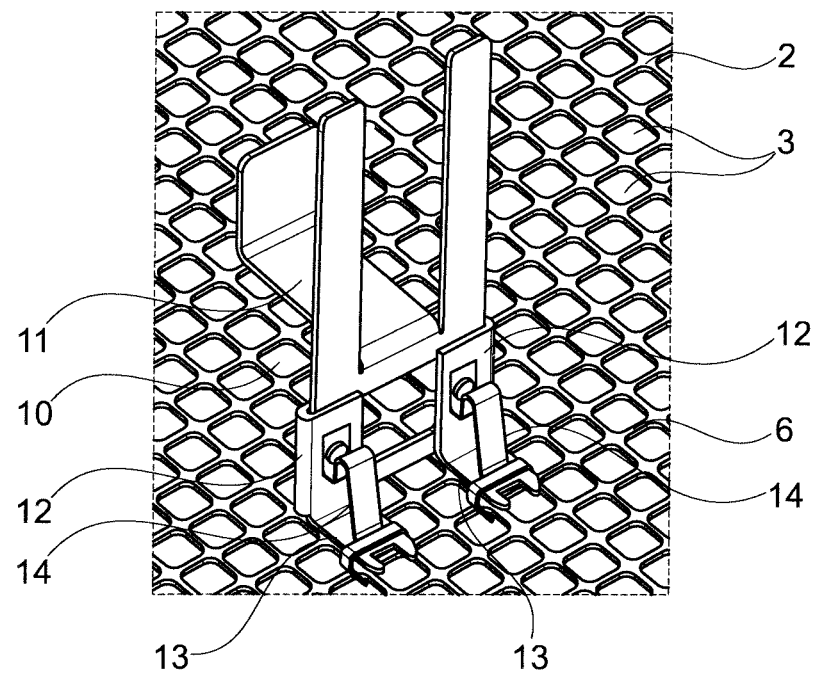
FIG. 2B is a front view of a mounting device according to the invention comprising a securing device according to the invention which is fixed in the perforated base of a mesh basket.
Figure 3:
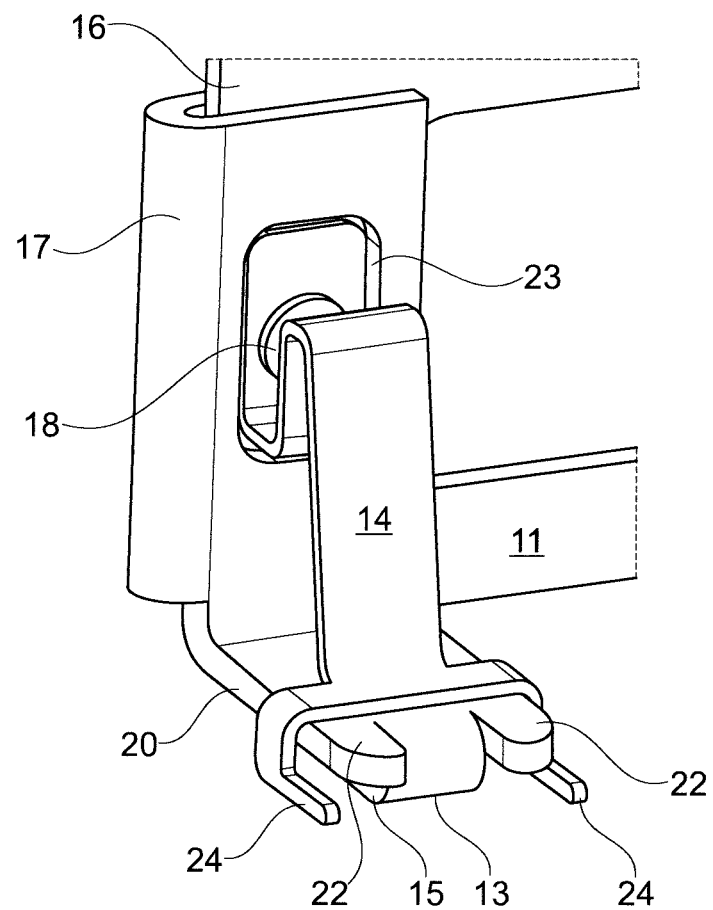
FIG. 3 shows a close-up of a securing device according to the invention.
Figure 4:
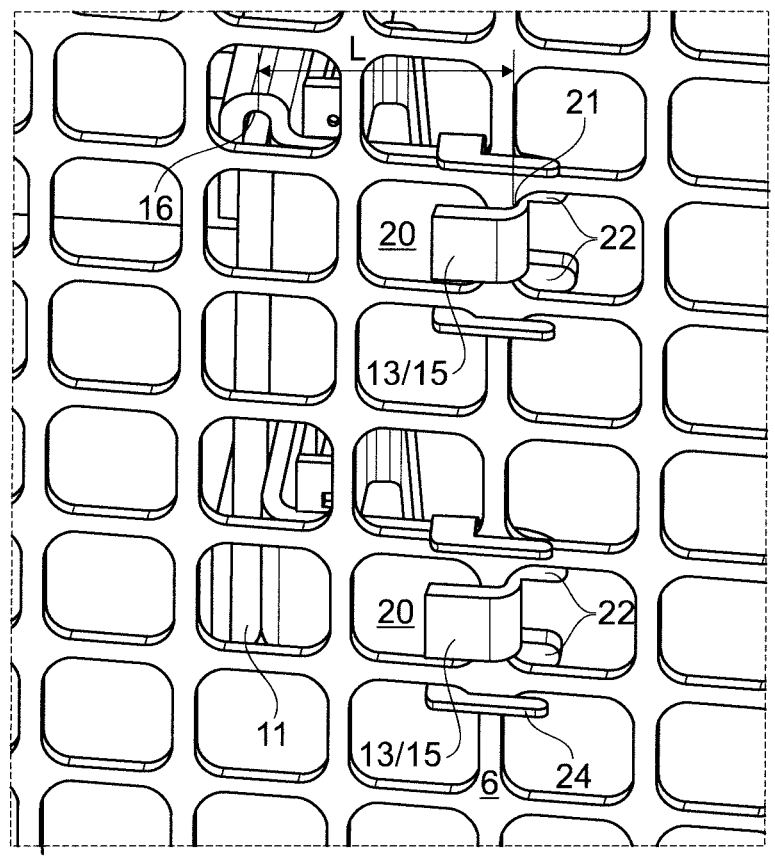
FIG. 4 is a view of a mounting device according to the invention from below, in the state when secured to the mesh basket.

Due to the above disadvantages and other disadvantages known from prior art, the preferred object of the mounting device 10 according to the invention shown in FIGS. 2 to 4 and fastened by means of securing devices 12, or of a mesh basket system according to the invention, is to provide a modular mounting system in which the mounting devices 10 are fixed on the base of the mesh basket 1 by means of securing devices 12, with little effort and without any tools, and which will be described in more detail in the following by means of a preferred embodiment. In this way, depositing devices 11 for individual products/product groups can be manufactured and stored. These can be assembled quickly, easily and in modular fashion into a set by using the securing devices 12 according to the invention.

According to the exemplary embodiment shown, a mounting device 10 of the invention basically has a depositing device 11 and a number of (here two) securing devices 12. The depositing devices 11, as is known from the state of the art, can adopt a multitude of embodiments, can be individually adapted to the sterile products to be stored on them and, according to the invention, only have to be adapted to be received directly or indirectly by one or more securing devices 12 or to be arranged on them. The securing devices 12 shown are adapted to engage in any neighboring recesses 3 of the illustrated sieve-like/perforated base 2 (engage around any lattice bar) and can be fixed to it theoretically in any spatial direction. The shown embodiment thus allows to arrange/immobilize a multitude of embodiments of the depositing devices 11 with a relatively small number of variants of the securing devices 12 (here two, one left-hand and one right-hand securing device for each front side of the depositing device 11 which is of web-like design here), which can be positioned almost arbitrarily on the base 2 of the mesh basket 1. In other words, the securing devices 12 according to the invention can be used for mesh baskets and for other types of depositing devices as well. In addition, the illustrated embodiment of the securing device 12 requires only a few (three) adjacent recesses 3 to be mounted on the container base 2.

In the embodiment shown, the securing device 12 has a substantially L-shaped geometry or an L-shaped supporting base 16. In the vertical section of the L-shape of the supporting base 16, a holding section 17 for a depositing device 11 is provided, whereas the lower section of the L-shape forms support area 20. At the distal end of the support area 20, the securing device 12 forms a first securing section 13, which is adapted to produce a form-fitting engagement with the edge of a recess 3 in the container base 2, in this example by an approximately U-shaped bent section or hook 15 at the underside of the distal end of the support area 20. Due to the U-shape of the first holding section 13 and the perforated sieve structure of the base 2, the securing device 12, having been brought into engagement in the recess 3, can be released from this engagement only by a movement in a preferential direction. A second securing section 14 of the securing device 12 in the example shown is designed as a spring element made of a spring metal sheet which is clamped/tensioned between the front side or the side of the vertical section of the L-shape facing the foot and opposite edges of recesses 3 in the base 2, so that the securing device 12 is pressed contrary to the preferential direction and thus anchored with the perforation 3. The engagement of the second securing section 14 in the perforation 3 of the base 2 in the example shown is constructed in such a way that the spring plate branches out in distal direction and forms two fork prongs 24 which come into engagement beneath adjacent recesses 3 on the left and right side of the support area 20 and thus generate—in addition to the clamping effect with the edges the perforation 2—a further form fit which is opposite to the direction of the form fit generated by the first securing section 13. Due to the mentioned constructional features, the securing device 12 shown is designed to engage in few adjacent recesses 3 and still be able to offer a comparatively high stability. In the embodiment shown, the fork prongs also have the function to encompass two lattice bars 6 or two edges of recesses 3 running parallel to the preferential direction or receive these between them and thereby create a form fit transverse to the preferential direction.

A preferred aim of the illustrated mounting according to the invention is to provide a comparatively high stability or a comparatively low play compared to a tilting of the securing device in the fixed state. For this purpose, the holding section 17 for the depositing device 11 and the first securing section 13 are arranged at opposite ends of the support area 20 and thus spaced apart (L) in a plane parallel to that of the base 2, thus increasing the stability against tilting along the proximal edge of the L-shape of the securing device. In particular, this spacing (L) also increases the lever arm of the bearing force at a point of engagement 21 at which the first securing section 13 engages in the perforation 3 of the base 2, compared to a sterile product preferably supported (with its center of gravity) on the opposite side of the mounting.

Tilting in the other direction, i.e. over the distal end edge the L-shape of securing device 12, is constructionally minimized by the fact that the support area 20 extends beyond the point of engagement 21 like a fork prong, whereby the end edge of the support area 20 is displaced in distal direction and the distal fork prongs 24 of the second securing section 14 form a counter bearing for such a tilting movement by engaging underneath the adjacent recesses 3. In addition, said fork prongs 24 of the second securing section 14, by engaging in recesses 3 which are oriented transverse to the longitudinal direction of the support area 20 and are adjacent thereto, create a stability against tilting in said transverse direction.

As can be clearly seen in FIGS. 2A and 2B, the securing devices have 12 holding sections 17 which in their cross-section are substantially U-shaped as a bent section, said U-shaped legs embracing the end faces the web-like or plate-like underside of the depositing device 11 or holding these in a form-fitting manner. The resulting form fit can significantly increase the stiffness/stability of the connection between the depositing device 11 and the securing device 12; moreover, the bag-like end of the opening of the U-shape can also serve as a lateral stop.

In the exemplary embodiment shown, the depositing device 11 is additionally held in the securing device 12 by a pin/hole connection 18, 19, thus preventing the depositing device from being pulled out or released from the U-shaped enclosure by the securing device 12. As can be seen particularly clearly in the detailed view shown in FIG. 3, the second securing section 14 in the fixed state exerts a pressing force on the depositing device 11 by reaching through a recess 23 in a U-leg of the holding section 17 and pressing the depositing device 11 against the second U-leg behind it. This combination of complete faun fit by the U-shaped seat 17 and the pin 18 with additional frictional connection by the spring element 14 allows a higher stability of the connection in comparison to solutions as known from the state of the art.

The second securing section 14 is detachably connected to the securing device 12 in the example shown and is retained on the securing device via the pin 18 in a form-fitting manner and via its internal elastic restoring forces in a force-fitting fashion. A modular design of the second securing section 14 can facilitate the attachment of the securing device 12 to the base 2 as well as the detachment from it and enables an exchange of the second securing section 14, e.g. in case of a defect or to adapt it to a different mesh structure of another mesh basket 1.

The securing device 12 shown as an example is made of a medically compatible metal, but it is also possible to use a plastic material which is suitable for sterilization.

Based on the exemplary embodiment shown, the securing device 12 according to the invention can be modified in many ways.

By way of example, the invention can also be used as a fastening solution for sieve-like or lattice-shaped surfaces apart from medical applications.

Also the shown combination of recesses 3, where the securing sections 13, 14 are in engagement, can be varied almost in any desired way; also the number of securing devices 12 serving for fixing a depositing device 11 can be varied, and it is also conceivable, for example, that a single securing device 12 serves to securely fasten a depositing device 11.

The invention claimed is:

1. A securing device of a sterile product mounting for securing the sterile product mounting in a medical container, the securing device comprising:
   a supporting base which is provided for supporting/receiving the sterile product mounting and has an undercut portion as a fixed bearing acting in a first direction and designed to come into latching engagement with a corresponding undercut on the medical container;
   an undercut element as a floating bearing and movably retained in a direct or indirect fashion on the supporting base, said floating bearing acting in a second direction opposite the first direction of the undercut portion and being designed to be brought into a latching engagement with the medical container; and
   a spring element or a spring portion provided on the undercut element or on the supporting base, which is designed to bias the undercut element in the second direction while being directly or indirectly supported on the supporting base,
   the undercut portion being U-shaped or hook-shaped and designed to engage around an edge of a first recess provided on a base of the medical container in a form-fitting manner,
   the undercut element being designed to engage around the edge of the first recess or of at least one second recess in a form-fitting manner from an opposite direction, and
   at least one of said undercut portion and said undercut element being spring-elastic,
   wherein the medical container has a sieve- or lattice-shaped base and the undercut portion is designed to engage around a lattice bar in a form-fitting manner, whereas the undercut element is designed to engage around said lattice bar in a form-fitting manner from an opposite direction.

2. The securing device according to claim 1, wherein the supporting base of the securing device comprises a holding section to which the mounting is secured or can be secured on one of its ends and both the undercut portion and the undercut element are located at an opposite end of the supporting base such that, in a state in which the mounting is secured to the medical container by the securing device, both the undercut portion and the undercut element engage in recesses in the base of the medical container distanced substantially in the same direction with respect to the holding section.

3. The securing device according to claim 1, wherein the undercut portion is configured to be inserted in the first recess and can be moved to a securing position, in which a securing section engages around the edge of the first recess or the lattice bar in a form-fitting manner such that the undercut portion can be released from the form-fitting manner only by a movement in a preferential direction and the undercut element is designed to be spring-elastic and can be made to engage in recesses such that the securing device is acted upon with a spring force contrary to the preferential direction.

4. The securing device according to claim 3, wherein the undercut element produces a form fit transverse to the preferential direction by resting in a secured state against at least two edges of one or more recesses.

5. The securing device according to claim 4, wherein the undercut element is designed to be shaped as a fork and laterally engages around the undercut portion.

6. The securing device according to claim 1, wherein the undercut portion and the undercut element are arranged inside the medical container in a secured state and engage in the recesses from inside the medical container, whereby the securing device is detachable from the medical container by an access exclusively from inside the medical container.

7. A mounting device for arranging/receiving sterile products or products to be sterilized in the interior of a medical container which comprises a base having a number of recesses, the mounting device comprising:
   a sterile product mounting for holding or receiving sterile products or products to be sterilized; and
   at least two securing devices according to claim 1, wherein the sterile product mounting can be releasably secured without tools at each of its end faces with a securing device, and the securing devices are adapted to receive different sterile product mountings which for their part are adapted to receive various sterile products.

8. A modular mesh basket system for arranging/receiving sterile products or products to be sterilized, the modular mesh basket system comprising:

a mesh basket comprising an interior defined by a base and side walls and having a number of recesses in the base; and a number of mounting devices that can be brought into engagement with the recesses and are built up in modular fashion from sterile product mountings and securing devices according to claim 1, wherein for individually loading the mesh basket, the securing devices can be made to engage different recesses in a flexible manner and are adapted to receive/immobilize various sterile product mountings which for their part are adapted to receive various sterile products.

9. A securing device of a sterile product mounting for securing a sterile product in a medical container, the securing device comprising:

a supporting base which is provided for supporting the sterile product mounting and has an undercut portion as a fixed bearing acting in a first direction and designed to come into latching engagement with a corresponding undercut on the medical container;

an undercut element as a floating bearing and movably retained in a direct or indirect fashion on the supporting base, said floating bearing acting in a second direction opposite the first direction of the undercut portion and being designed to be brought into a latching engagement with a corresponding undercut on the medical container;

a spring element or a spring portion provided on the undercut element or on the supporting base, which is designed to bias the undercut element in the second direction while being directly or indirectly supported on the supporting base; and a holding section which is provided on the supporting base and designed to hold the sterile product mounting in a form-fitting manner, and which is designed such that the mounting is insertable into the holding section perpendicular to an extending direction of the base of the medical container when the supporting base is secured on a base of the medical container, wherein the securing device forms a support area which rests upon the base of the medical container and the support area forms at least one extension which projects beyond the undercut portion in a direction facing away from a holding section and is adapted to have a supporting contact with the base of the medical container such that tilting of the securing device is prevented.

10. The securing device according to claim 9, wherein the holding section is designed as a sheet metal bent section which has substantially U-profile-shaped legs between which the sterile product mounting can be inserted and held.

11. The securing device according to claim 9, wherein the undercut element is designed to function as the spring element and has one of its end portions designed so as to make a form fit with the medical container and has its other end portion designed so as to be supported by the sterile product mounting retained in the holding section, thus clamping the sterile product mounting in place in the holding section.

12. The securing device according to claim 9, wherein the medical container has a sieve- or lattice-shaped base and the undercut portion is designed to engage around a lattice bar in a form-fitting manner, whereas the undercut element is designed to engage around said lattice bar in a form-fitting manner from an opposite direction.

13. The securing device according to claim 9, wherein the undercut portion is configured to be inserted in the first recess and can be moved to a securing position, in which a securing section engages around the edge of the first recess or the lattice bar in a form-fitting manner such that the undercut portion can be released from the form fit only by a movement in a preferential direction and the undercut element is designed to be spring-elastic and can be made to engage in recesses such that the securing device is acted upon with a spring force contrary to the preferential direction.

14. The securing device according to claim 9, wherein the undercut portion and the undercut element are arranged in the medical container inside in a secured state and engage in the recesses from inside the medical container, whereby the securing device is detachable from the medical container by an access exclusively from inside the medical container.

15. A mounting device for arranging/receiving sterile products or products to be sterilized in the interior of a medical container which comprises a base having a number of recesses, the mounting device comprising:

a sterile product mounting for holding or receiving sterile products or products to be sterilized; and at least two securing devices according to claim 9, wherein the sterile product mounting can be releasably secured without tools at each of its end faces with a securing device, and the securing devices are adapted to receive different sterile product mountings which for their part are adapted to receive various sterile products.

16. A securing device of a sterile product mounting for securing the sterile product mounting in a medical container, the securing device comprising:

a supporting base which is provided for supporting/receiving the sterile product mounting and has an undercut portion as a fixed bearing acting in a first direction and designed to come into latching engagement with a corresponding undercut on the medical container;

an undercut element as a floating bearing and movably retained in a direct or indirect fashion on the supporting base, said floating bearing acting in a second direction opposite the first direction of the undercut portion and being designed to be brought into a latching engagement with a corresponding undercut on the medical container; and a spring element or a spring portion provided on the undercut element or on the supporting base, which is designed to bias the undercut element in the second direction while being directly or indirectly supported on the supporting base, wherein the undercut portion is configured to be inserted in the first recess and can be moved to a securing position, in which a securing section engages around the edge of the first recess or a lattice bar in a form-fitting manner such that the undercut portion can be released from the form fit only by a movement in a preferential direction and the undercut element is designed to be spring-elastic and can be made to engage in recesses such that the securing device is acted upon with a spring force contrary to the preferential direction, and wherein the undercut element produces a form fit transverse to the preferential direction by resting in a secured state against at least two edges of one or more recesses.

17. The securing device according to claim 16, wherein the undercut element is designed to be shaped as a fork and laterally engages around the undercut portion.

18. The securing device according to claim 16, wherein the undercut portion being U-shaped or hook-shaped and designed to engage around an edge of a first recess provided on the base of the medical container in a form-fitting manner, the undercut element being designed to engage around the edge of the first recess or of at least one second recess in a form-fitting manner from an opposite direction, and at least one of said undercut portion and said undercut element being spring-elastic.

19. A securing device of a sterile product mounting for securing a sterile product in a medical container, the securing device comprising:

a supporting base which is provided for supporting the sterile product mounting and has an undercut portion as a fixed bearing acting in a first direction and designed to come into latching engagement with a corresponding undercut on the medical container;

an undercut element as a floating bearing and movably retained in a direct or indirect fashion on the supporting base, said floating bearing acting in a second direction opposite the first direction of the undercut portion and being designed to be brought into a latching engagement with a corresponding undercut on the medical container;

a spring element or a spring portion provided on the undercut element or on a supporting base, which is designed to bias the undercut element in the second direction while being directly or indirectly supported on the supporting base; and a holding section which is provided on the supporting base and designed to hold the sterile product mounting in a form-fitting manner, and which is designed such that the mounting, when the supporting base is secured on the base of the medical container, can be inserted into the holding section perpendicular to a extending direction of the base, wherein the medical container has a sieve- or lattice-shaped base and the undercut portion is designed to engage around a lattice bar in a form-fitting manner, whereas the undercut element is designed to engage around said lattice bar in a form-fitting manner from an opposite direction.

* * * * *